United States Patent [19]
Fischer et al.

[11] Patent Number: 5,905,159
[45] Date of Patent: May 18, 1999

[54] METHOD OF PRODUCING 1,4-BUTANEDIOL AND TETRAHYDROFURAN FROM FURAN

[75] Inventors: Rolf Fischer, Heidelberg; Rolf Pinkos, Bad Dürkheim, both of Germany

[73] Assignee: BASF Aktiengesellschaft, Ludwigshafen, Germany

[21] Appl. No.: 08/913,440

[22] PCT Filed: Mar. 21, 1996

[86] PCT No.: PCT/EP96/01247

§ 371 Date: Sep. 16, 1997

§ 102(e) Date: Sep. 16, 1997

[87] PCT Pub. No.: WO96/29322

PCT Pub. Date: Sep. 26, 1996

[30] Foreign Application Priority Data

Mar. 22, 1995 [DE] Germany .......................... 195 10 438

[51] Int. Cl.⁶ .......................... C07D 307/08; C07C 27/00
[52] U.S. Cl. .......................... 549/429; 568/865
[58] Field of Search .......................... 568/865; 549/429

[56] References Cited

U.S. PATENT DOCUMENTS

| 3,021,342 | 2/1962 | Manly | 549/356 |
| 4,146,741 | 3/1979 | Prichard | 568/865 |
| 4,475,004 | 10/1984 | Nalepa | 568/865 |
| 4,476,332 | 10/1984 | Nalepa | 568/865 |

OTHER PUBLICATIONS

Ind. Eng. Chem. Prod. Res. Dev., vol. 12, No. 4, 1973.

*Primary Examiner*—Amelia Owens
*Attorney, Agent, or Firm*—Keil & Weinkauf

[57] ABSTRACT

1,4-butanediol and THF are prepared from furan by a process which comprises converting furan in the presence of water and hydrogen but in the absence of a water-soluble acid in a single stage over a hydrogenation catalyst, the hydrogenation catalyst containing at least one element of subgroup I, V, VI, VII or VIII in the form of a compound or in elemental form and the restriction that the catalyst does not contain nickel alone being applicable.

18 Claims, No Drawings

METHOD OF PRODUCING 1,4-BUTANEDIOL AND TETRAHYDROFURAN FROM FURAN

This application is a 371 of PCT/EP96/01247 filed Mar. 21, 1996

The present invention relates to a process for the preparation of 1,4-butanediol/tetrahydrofuran (THF) from furan.

In Russian Patent 114,928, furan in neutral or slightly acidic, aqueous solution (addition of formic acid) is hydrogenated over nickel catalysts to give a mixture of tetrahydrofuran, 1,4-butanediol and small amounts of n-butanol. The yields of butanediol/THF are modest, with low conversions. J. M. Watson, Ind. Eng. Chem. Prod. Res. Develop. 12 (4) (1973), 310–311, describes the same reaction over nickel catalysts but in the presence of acetic acid. U.S. Pat. No. 4,146,741 likewise describes the hydrogenation of furan to butanediol over nickel catalysts, which may also contain copper, but in the presence of aqueous dicarboxylic acid solutions. It is also stated that, if the acidity of the reaction system is too low, virtually only THF and only a small amount of diol is formed. In U.S. Pat. No. 4,475,004, halogenated carboxylic acids are used in addition to nickel catalysts. In the absence of these halogenated carboxylic acids, butanediol is formed only in traces. The same halogenated carboxylic acids are also used in U.S. Pat. No. 4,476,332, in combination with ruthenium catalysts. Without these acid promoters, no butanediol is formed.

The abovementioned methods for the preparation of 1,4-butanediol and THF from furan have the disadvantage that they generally give only low yields of butanediol and result in the formation of byproducts (e.g. butanediol diacetate) which are difficult to separate from the desired product. In general, it is true that one catalyst component (carboxylic acid) makes it much more difficult to carry out continuously the reactions described above is on an industrial scale. This is because, on the one hand, precautions must be taken to avoid corrosion of the plants (the use of halocarboxylic acids is virtually ruled out). On the other hand, the acids must be discharged with the product stream and continuously recycled after expensive isolation. Since a certain degree of esterification always takes place in the presence of an acid and of an alcohol (butanediol), some of the carboxylic acid must be continuously replenished. Moreover, hydrogenation of the acid is to be expected during the reaction, likewise leading to continuous losses of carboxylic acids.

It is an object of the present invention to provide a process which on the one hand leads to high selectivity with respect to butanediol/THF and on the other hand manages without promoters, such as the stated carboxylic acids.

We have found that this object is achieved by a process for the preparation of 1,4-butanediol/THF from furan, which is converted as a reaction mixture with water and in the presence of hydrogen but in the absence of a water-soluble acid or carboxylic acid, at 20–300° C. and 100 kPa 30 MPa (1–300 bar) over a hydrogenation catalyst. This hydrogenation catalyst contains at least one of the elements of subgroup I, V, VI, VII or VIII of the Periodic Table of Elements in the form of a compound, preferably as an oxide, or in elemental form, the additional restriction that it does not contain nickel alone being applicable.

In carrying out the novel process, furan is reacted with water in general in a molar furan/water ratio of from 1:0.1 to 1:100, preferably from 1:0.2 to 1:50, particularly preferably from 1:1 to 1:10, to give 1,4-butanediol/THF. This is effected in the presence of hydrogen and a hydrogenation catalyst at in general 100 kPa–30 MPA (1–300 bar), preferably 500 kPa–20 MPa (5–200 bar), particularly preferably 1–15 MPa (10–150 bar), and at from 20 to 300° C., preferably from 40 to 230° C., particularly preferably from 80 to 200° C.

In the novel process, the ratios of the yields of butanediol to those of THF are in general 0.1–40, preferably 0.2–35, particularly preferably 0.5–25, based on the mass.

In general, all catalysts which are suitable for the hydrogenation of carbonyl groups and contain at least one of the elements of subgroup I, V, VI, VII or VIII of the periodic table (except for Ni alone) may be used as hydrogenation catalysts for the novel process. The catalysts may be in the form of fixed-bed catalysts, suspended catalysts or homogeneously dissolved catalysts.

The catalytically active metal of subgroups I and/or V and/or VI and/or VII and/or VIII (except for Ni alone) or a compound thereof may be present as a mixture or alloy with further metals/elements of subgroup I and/or V and/or VI and/or VII and/or VIII and/or main groups III and/or IV.

Heterogeneous catalysts which are preferably present as metals in activated, finely divided form having a large surface area are preferred. Preferred examples of these are an Ru sponge or mixtures of two or more metals, as formed, for example, by reduction of corresponding metal salts and/or other metal compounds together, in particular an Re/Ru sponge after reduction of an aqueous $Re_2O_7/RuCl_3$ solution.

Furthermore, precipitated catalysts may advantageously be used for the novel process. Such catalysts can be prepared by precipitating their catalytically active components from salt solutions thereof, in particular from the solutions of nitrates and/or acetates thereof, for example by adding alkali metal and/or alkaline earth metal hydroxide and/or carbonate solutions, as, for example, sparingly soluble hydroxides, hydrated oxides, basic salts or carbonates. The precipitates obtained are then dried and thereafter converted by calcination at in general from 300 to 700° C. into the corresponding oxides, mixed oxides and/or mixed-valency oxides which are reduced to the relevant metals and/or oxide compounds of lower oxidation state by a treatment with hydrogen or with hydrogen-containing gases and, as a rule, from 100 to 400° C. and converted into the actual catalytically reactive form. As a rule, reduction is continued until no further water is formed. In the preparation of precipitated catalysts which contain a carrier, precipitation of the catalytically active components may be effected in the presence of the relevant carrier. However, the catalytically active components may advantageously also be precipitated simultaneously with the carrier from the relevant salt solutions.

For the novel process, it is preferable to use hydrogenation catalysts which contain the metals or metal compounds which catalyze the hydrogenation as a precipitate on a carrier. In addition to the abovementioned precipitation catalysts which contain a carrier in addition to the catalytically active components, supported catalysts in which the components which catalyze the hydrogenation have been applied to the carrier, for example by impregnation, are suitable for the novel process.

The method of application of the catalytically active metals or metal compounds to the carrier is as a rule not critical and may be effected in a wide range of ways. The catalytically active metals or metal compounds can be applied to these carriers, for example, by impregnation of the carrier with solutions or suspensions of the salts or oxides of the relevant elements, drying and subsequent reduction of the metal compound to the relevant metals or compounds of lower oxidation states by means of a reducing agent, preferably hydrogen or complex hydrides. Another possibility for applying the catalytically active metals or metal compounds to the carrier is to impregnate the latter with a solution of thermally readily decomposable complexes, for example with carbonyl or hydrido complexes of the catalytically active metals, and to heat the carrier thus impregnated to, for example, 300 to 600° C. for thermal decomposition of the absorbed metal compounds. The catalytically active metals or metal compounds may furthermore be deposited on the catalyst carrier by vapor deposition or by flame spraying.

The content of catalytically active metals/metal compounds in these supported catalysts is in principle not critical for the success of the novel process. It is evident to a person skilled in the art that higher contents of catalytically active metals/metal compounds in these supported catalysts lead to higher space-time yields than lower contents. In general, however, supported catalysts whose content of catalytically active metals/metal compounds is from 0.1 to 80, preferably from 0.5 to 30, % by weight, based on the total catalyst, are used. Since these stated contents are based on the total catalyst, including the carrier, but the different carriers have very different densities and specific surface areas, the contents may exceed or fall below the stated contents without there being any adverse effect on the result of the novel process. Preferably, a plurality of the catalytically active metals/metal compounds are applied to the particular carrier. These may be applied to the carrier simultaneously or in succession. Furthermore, the catalytically active metals/metal compounds may be applied to the carrier, for example, by the methods disclosed in DE-A 25 19 817, EP-A 0 147 219 and EP-A 0 285 420. In the catalysts of the abovementioned publications, the catalytically active metals/metal compounds are present as alloys which are produced by thermal treatment and/or reduction of the abovementioned salts or complexes applied, for example, by impregnation.

Further variants of preferred catalyst systems are described, for example, in JP 59 184 138 and DE 42 00 247.8. Water-soluble or nonsoluble, inorganic assistants are concomitantly introduced into the system (eg. zinc oxide, zinc sulfate, zinc hydroxide or nickel sulfate).

The activation of both the precipitated catalysts and the supported catalysts can be carried out in situ at the beginning of the reaction by the hydrogen present. Preferably, however, these catalysts are activated separately before they are used.

In general, the oxides of aluminum and of titanium, zirconium dioxide, silica, aluminas, such as montmorillonite, silicates, such as magnesium or aluminum silicates, zeolites, such as ZSM-5 or ZSM-10 zeolites and active carbon may be used as carriers. Preferred carriers are aluminas, titanium oxides, silica, zirconium dioxide and active carbon. Mixtures of different carriers can of course also serve as carriers for the catalysts which can be used in the novel process. Active carbon carriers are particularly preferably used.

The following may be mentioned by way of example as heterogeneous catalysts which can be used in the novel process:

Ruthenium sponge, rhenium sponge, ruthenium/rhenium sponge, ruthenium on active carbon, rhenium on active carbon, rhenium on silica, rhenium/tin on active carbon, ruthenium/palladium on active carbon, rhenium/copper on active carbon, rhenium/nickel on active carbon, ruthenium/nickel on active carbon, rhenium/ruthenium on active carbon, cobalt/rhenium on active carbon, ruthenium/copper on active carbon, copper/nickel on active carbon, copper/ ruthenium on active carbon, copper on active carbon, copper on silica, copper on alumina, copper chromide and barium copper chromide.

The homogeneous catalysts used may be those described for example, in Houben-Weyl, Methoden der organischen Chemie, vol. IV/1c, pages 45 to 67, Thieme Verlag, Stuttgart 1980. Preferred homogeneous catalysts. are in particular the complexes of rhodium, of ruthenium and of cobalt with phosphine or phosphite ligands, the preparation of which is described, for example in CA 72 76 41, H. Brunner in Hartley: The Chemistry of the Metal-Carbon Bond; vol. 5, pages 110–124, John Wiley & Sons, New York, and in Toth et al., Inorg. Chem. Acta 42, (1980), 153, and in the literature cited therein.

The novel process can be carried out both continuously and batchwise. For example, tube reactors in which the catalyst is advantageously arranged in the form of a fixed bed via which the reaction mixture can be passed by the liquid phase or trickle-bed procedure can advantageously be used for the continuous procedure.

Simple stirred reactors can be used for batchwise procedure. However, it is preferable to use loop reactors. The catalyst is advantageously arranged in the form of a fixed bed. In the case of incomplete reaction of the starting material, the latter is advantageously recycled into the reaction, either after separation of the desired product by distillation or as a part-stream together with the other reaction products. This proves to be particularly advantageous in the continuous procedure.

The novel process can advantageously be carried out in the presence of a solvent which is inert (under the reaction conditions, for example with water-soluble ethers, such as tetrahydrofuran, dioxane or diethylene glycol dimethyl ether. Alcohols, in particular the product 1,4-butanediol, can also advantageously be used as solvents.

The reacted mixture discharged from the novel process is advantageously worked up by distillation, and, in addition to the products 1,4-butanediol and THF, the compounds gamma-butyrolactone and n-butanol obtained as byproducts can be recovered as further desired products.

The starting material furan can readily be prepared, for example by decarbonylation or furfural.

1,4-butanediol is prepared worldwide in large amounts and serves as a diol component for the preparation of, inter alia, polyesters, polyurethanes and epoxy resins. THF is used, for example, as a solvent or for the preparation of polytetrahydrofuran.

Further preferred embodiments of the present invention are described below in the examples and in the dependent claims.

EXAMPLES

Example 1

0.5 g of a rhenium/ruthenium/active carbon catalysts (5% by weight of rhenium and 1% by weight of ruthenium, based in each case on the total weight of the catalyst), 1.3 g of furan and 5 g of water were introduced into a 50 ml metal autoclave having a stirrer. The catalyst had been prepared beforehand by impregnation of the active carbon with an aqueous $Re_2O_7/RuCl_3$ solution, drying at 120° C. and activation for two hours in a hydrogen stream at 300° C. A pressure of 3 MPa (30 bar) was generated in the autoclave by forcing in hydrogen. The autoclave was then heated at 160° C. for 3 hours. Thereafter, the autoclave was cooled to room temperature and was let down at a residual pressure of about 1.8 MPa (18 bar). At a conversion of 99%, the following yields determined by gas chromatography were obtained: 24% of THF, 68% of 1,4-butanediol, 2% of butyrolactone and 5% of n-butanol (these stated percentages as well as those in all examples below are by weight).

Example 2

1.35 g of furan were converted over an Ru/active carbon catalyst (1% by weight, based on the total weight of the catalyst, of ruthenium, prepared by impregnation of the active carbon with an aqueous $RuCl_3$ solution, drying and activation as in Example 1) during a residence time of 1.5 hours, similarly to Example 1. At a conversion of 97%, the following yields determined by gas chromatography were obtained: 51% of THF, 33% of 1,4-butanediol and 12% of n-butanol.

Example 3

1.52 g of furan were converted over a Co/Re active carbon catalyst (3% by weight of cobalt and 3% by weight of rhenium, based in each case on the total weight of the catalyst, prepared by impregnation of the active carbon with an aqueous $Co(OAc)_2/Re_2O_7$ solution, impregnation and activation as in Example 1) during a residence time of 2 hours, similarly to Example 1. At a conversion of 80%, the following yields determined by gas chromatography were obtained: 30% of THF, 33% of 1,4-butanediol, 10% of n-butanol and 1% of butyrolactone.

Example 4

1.4 g of furan were converted over an Ru/Cu/active carbon catalyst (3% by weight of ruthenium and 3% by weight of copper, based in each case on the total weight of the catalyst, prepared by impregnation of the active carbon with an aqueous $RuCl_3/Cu(OAc)_2$ solution, drying and activation as in Example 1) during a residence time of 3 hours, similarly to Example 1. At a conversion of 89%, the following yields determined by gas chromatography were obtained: 50% of THF, 31% of 1,4-butanediol, 5% of n-butanol and 1% of butyrolactone.

Example 5

1.4 g of furan were converted over an Re/Ni/active carbon catalyst (5% by weight of rhenium and 5% by weight of nickel, based in each case on the total weight of the catalyst, prepared by impregnation of the active carbon with an aqueous $Re_2O_7/Ni(OAc)_2$ solution, drying and activation as in Example 1) during a residence time of 2 hours, similarly to Example 1. At a conversion of 99%, the following yields determined by gas chromatography were obtained: 58% of THF, 36% of 1,4-butanediol, 3% of n-butanol and 1% of butyrolactone.

Example 6

1.44 g of furan were converted over an Rh/Re/active carbon catalyst (1% by weight of rhodium and 5% by weight of rhenium, based in each case on the total weight of the catalyst, prepared by impregnation of the active carbon with an aqueous $RhCl_3/Re_2O_7$ solution, drying and activation as in Example 1) during a residence time of 0.75 hours, similarly to Example 1. At a conversion of 100%, the following yields determined by gas chromatography were obtained: 75% of THF, 18% of 1,4-butanediol, 2% of n-butanol and 1% of butyrolactone.

Example 7

1.52 g of furan were converted over an Ni/Cu/active carbon catalyst (3% by weight of nickel and 3% by weight of copper, based in each case on the total weight of the catalyst, prepared by impregnation of the active carbon with an aqueous $Ni(OAc)_2/Cu(OAc)_2$ solution, drying and activation as in Example 1) during a residence time of 1.5 hours, similarly to Example 1. At a conversion of 100%, the following yields determined by gas chromatography were obtained: 65% of THF, 32% of 1,4-butanediol, 1% of n-butanol and 1% of butyrolactone.

Example 8

1.4 g of furan were converted over an Ru/Ni active carbon catalyst (1% by weight of ruthenium and 4% by weight of nickel, based in each case on the total weight of the catalyst, prepared by impregnation of the active carbon with an aqueous $RuCl_3/Ni(OAc)_2$ solution, drying and activation as in Example 1) during a residence time of 2 hours, similarly to Example 1. At a conversion of about 60%, the following yields determined by gas chromatography were obtained: 48% of THF, 10% of 1,4-butanediol and 2% of n-butanol.

Example 9

The experiment from Example 8 was repeated in the presence of 1 g of $NiSO_4 \cdot 6H_2O$. At a conversion of 100%, the following yields determined by gas chromatography were obtained: 20% of THF, 70% of 1,4-butanediol and 7% of n-butanol.

Example 10

1.5 g of furan were converted over an Ru/Cu/Re/active carbon catalyst (1% by weight of ruthenium, 3% by weight of copper and 5% by weight of rhenium, based in each case on the total weight of the catalyst, prepared by impregnation of the active carbon with an aqueous $RuCl_3/Cu(OAc)_2/Re_2O_7$ solution, drying and activation as in example 1) at 170° C. and during a residence time of 3 hours, similarly to Example 1. At a conversion of 98%, the following yields determined by gas chromatography were obtained: 35% of THF, 53% of 1,4-butanediol, 7% of n-butanol and 3% of butyrolactone.

We claim:

1. A process for the preparation of 1,4-butanediol and tetrahydrofuran from furan, wherein furan is converted as a reaction mixture with water and in the presence of hydrogen but in the absence of a water-soluble acid in a single stage over a hydrogenation catalyst, the hydrogenation catalyst containing at least one element of subgroup I, V, VI, VII or VIII in the form of a compound or in elemental form, and the restriction that the catalyst does not contain nickel alone being applicable.

2. The process defined in claim 1, wherein the reaction is carried out at 20–300°C.

3. The process defined in claim 1, wherein the reaction is carried out at 0.1–30 MPa.

4. The process defined in claim 1, wherein wherein the starting materials furan and water are used in a molar ration of 1:0.1–1:100.

5. The process defined in claim 1, wherein the catalyst further contains an element of main group III or IV.

6. The process defined in claim 1, wherein the catalyst has been applied to a carrier by impregnation or precipitation, and the carrier is an oxide of aluminium or of titanium, $ZrO_2$, $SiO_2$, an alumina, a silicate, a zeolite, or active carbon.

7. The process defined in claim 1, wherein the catalyst contains ruthenium.

8. The process defined in claim 1, wherein the catalyst is a mixture or an alloy of elements of subgroup VI or VIII or a compound thereof.

9. The process defined in claim 1, wherein the catalyst is activated before being used.

10. The process defined in claim 1, wherein the active component of the catalyst amounts for 0.1–80% by weight, based on the total weight of the catalyst.

11. The process defined in claim 1, which is carried out at 40–230° C.

12. The process defined in claim 1, which is carried out at 80–200° C.

13. The process defined in claim 1, which is carried out at 0.5–20 MPa.

14. The process defined in claim 1, which is carried out at 1–15 MPa.

15. The process defined in claim 1, wherein wherein the starting materials furan and water are used in a molar ration of 1:0.2–1:50.

16. The process defined in claim 1, wherein wherein the starting materials furan and water are used in a molar ration of 1:1–1:10.

17. The process defined in claim 6, wherein the catalyst has been applied to the montmorillonite, magnesium or aluminium silicate, ZSM-5 zeolite or ZSM-10 zeolite.

18. The process defined in claim 1, wherein the active component of the catalyst amounts for 0.5–30% by weight, based on the total weight of the catalyst.

* * * * *